US010279055B2

(12) United States Patent
Izrailit (10) Patent No.: US 10,279,055 B2
(45) Date of Patent: May 7, 2019

(54) POWER SUPPLY UNIT (71) Applicant: Tetra Laval Holdings & Finance S.A., Pully (CH)

(72) Inventor: Iosif Izrailit, Newton, MA (US)

(73) Assignee: TETRA LAVAL HOLDINGS & FINANCE S.A., Pully (CH)

( * ) Notice: Subject to any disclaimer, the term of this patent is extended or adjusted under 35 U.S.C. 154(b) by 182 days.

(21) Appl. No.: 15/119,966

(22) PCT Filed: Jan. 21, 2015

(86) PCT No.: PCT/EP2015/051065
§ 371 (c)(1),
(2) Date: Aug. 18, 2016

(87) PCT Pub. No.: WO2015/124354
PCT Pub. Date: Aug. 27, 2015

(65) Prior Publication Data
US 2017/0065734 A1    Mar. 9, 2017

(30) Foreign Application Priority Data

Feb. 19, 2014   (SE) ...................................... 1450195

(51) Int. Cl.
H05K 5/00          (2006.01)
H05K 7/00          (2006.01)
(Continued)

(52) U.S. Cl.
CPC .............. A61L 2/087 (2013.01); B65B 55/08 (2013.01); H05K 7/20463 (2013.01); H05K 1/11 (2013.01);
(Continued)

(58) Field of Classification Search
CPC ...... H05K 1/185; H05K 2201/10; H05K 1/11; H05K 2201/10151
(Continued)

(56) References Cited

U.S. PATENT DOCUMENTS 3,699,394 A    10/1972  Schuler
3,713,213 A *   1/1973  Cranston ................ B23K 20/08
                                              174/256
(Continued)

FOREIGN PATENT DOCUMENTS

CN    101557832 A    10/2009
JP    S47-011705 A    6/1972
(Continued)

OTHER PUBLICATIONS

International Search Report (PCT/ISA/210) dated Apr. 29, 2015, by the European Patent Office as the International Searching Authority for International Application No. PCT/EP2015/051065.
(Continued)

Primary Examiner — Binh B Tran
(74) Attorney, Agent, or Firm — Buchanan Ingersoll & Rooney PC (57) ABSTRACT Power supply unit, in particular for a sterilization device, comprising at least one electric component, wherein, at least one of the electric components is at least partly covered with a solid insulation layer, wherein the solid insulation layer is adapted to provide an electric insulation.

19 Claims, 6 Drawing Sheets (51) Int. Cl.
*H05K 1/18* (2006.01)
*A61L 2/08* (2006.01)
*H05K 7/20* (2006.01)
*B65B 55/08* (2006.01)
*H05K 3/28* (2006.01)
*H05K 1/11* (2006.01)

(52) U.S. Cl.
CPC ............ *H05K 1/185* (2013.01); *H05K 3/285* (2013.01); *H05K 2201/10* (2013.01); *H05K 2201/10151* (2013.01); *H05K 2203/1377* (2013.01)

(58) Field of Classification Search
USPC ........ 361/760–766, 782, 783; 174/260, 261; 257/207, 500, 502, 578, 691
See application file for complete search history.

(56) References Cited

U.S. PATENT DOCUMENTS

| | | |
|---|---|---|
| 4,120,017 A | 10/1978 | Sickles |
| 2008/0138243 A1 | 6/2008 | Kristiansson et al. |
| 2010/0202111 A1 | 8/2010 | Liang |
| 2012/0020463 A1 | 1/2012 | Cooley et al. |
| 2014/0232508 A1 | 8/2014 | Inaba |

FOREIGN PATENT DOCUMENTS

| | | |
|---|---|---|
| JP | S57-082890 U | 5/1982 |
| JP | S60-166290 U | 11/1985 |
| JP | H05-508298 A | 11/1993 |
| JP | 2003-185800 A | 7/2003 |
| JP | 2010-512284 A | 4/2010 |
| JP | 2013-093549 A | 5/2013 |
| WO | 92/19085 A1 | 10/1992 |
| WO | 2008/073015 A1 | 6/2008 |
| WO | WO 2013/004564 A1 | 1/2013 |

OTHER PUBLICATIONS

Written Opinion (PCT/ISA/237) dated Apr. 29, 2015, by the European Patent Office as the International Searching Authority for International Application No. PCT/EP2015/051065.

Office Action dated Sep. 16, 2014 by Swedish Patent Office in priority Swedish Application No. 1450195-1 filed on Feb. 19, 2014.

U.S. Appl. No. 15/120,079, filed Aug. 16, 2016.

Office Action (Notification of Reasons for Refusal) dated Dec. 25, 2018, by the Japanese Patent Office in corresponding Japanese Patent Application No. 2016-552895 and an English Translation of the Office Action. (7 pages).

* cited by examiner

POWER SUPPLY UNIT

This invention relates to a power supply unit, in particular for a sterilization device, to a sterilization device, in particular for packaging material and to an electric component, in particular to a voltage multiplier for said power supply unit.

Electron beam irradiation has been considered as a promising alternative for sterilizing purposes for which wet chemistry involving hydrogen peroxide has been the traditional technical platform. Electron beam irradiation provides sufficient sterilization of e. g. packaging material eliminating negative consequences of wet chemistry within e. g. a packaging machine. In this context, power supply unites are necessary to provide the high voltage that is used to operate one or more electron beam emitters. However, generating high voltage involves the problem of creating corona and arcs, e. g. inside the housing of the power supply unit. In particular, solutions have to be found to electrically insulate the electric components or parts, respectively, of the electric system inside the power supply unit. Known insulation techniques are in general heavy or require too much raw materials and supplies. In this context, in particular the weight of the power supply unit has to be considered as the case may be that the power supply unit is arranged at a movable mechanism. Furthermore, known insulation techniques are often not adapted to the requirements of the packaging industry. For example, an insulation technique which includes hazardous material or that may damage or pollute the material that has to be sterilized, such as packaging material for food, liquids or drugs is not suitable in such environments.

Therefore, there is a desire to provide a power supply unit, in particular for a sterilization device, a sterilization device, in particular for packaging material and an electric component, in particular a voltage multiplier, which maintains low weight and high cost effectiveness in combination with improved electric insulation properties.

The present application proposes a power supply unit according to claim 1, a sterilization device according to claim 12 and an electric component according to claim 13, all providing lower weight with improved electric insulation properties. Additional advantages and features of embodiments of the current invention are defined in the dependent claims.

According to the invention, a power supply unit, in particular for a sterilization device, comprises at least one electric component, characterized in that at least one of the electric components is at least partly covered with a solid insulation layer, wherein the solid insulation layer is adapted to provide an electric insulation. Generally, the power supply unit comprises an electric system adapted to provide a high output voltage, wherein the electric system comprises a plurality of electric components, wherein at least one of the electric components is at least partly covered with the solid insulation layer. Expediently, the electric system comprises power electronic components, high voltage components and control system components.

The term high voltage components refer to discrete or integrated components able to create, be operated in or handling high potentials or (if referred to the ground potential) high voltages. Power electronic components refer to components including solid-state electronics for the control and conversion of electric power.

The term insulation refers to a conductive separation between two elements. An insulator or isolator is, when used within its specification a substantially nonconductive element or material, being able to electrically separate to conductive elements from each other. An insulation layer consists of or comprises a material with a very high dielectric strength, thereby reducing the risk of leakage or stray current, coronas or arcs.

According to one or more embodiments, the different components are arranged in different chambers of the housing. This means that the housing comprises a first and at least one second chamber, wherein the power electronic components and the control system components are located e. g. within the second chamber and wherein the high voltage components are arranged e. g. in the first chamber. This allows the specific usage of appropriate insulation shields at and/or in the walls of the housing, in particular of the first chamber.

The power supply unit is connectable or connected, respectively, to an electron beam emitter via a high voltage output connector attached to the housing. Alternatively, also more than one electron beam emitter can be connected to one power supply unit. The combination of an electron beam emitter (or at least one) and the power supply unit is named sterilization device. Generally, the connection is a form and/or a force fit connection. The electron beam emitter comprises an electron generator for emitting charge carriers, such as electrons, along a path. The electron generator is generally enclosed in a hermetically sealed vacuum chamber. The vacuum chamber is provided according to one or more embodiments with an electron exit window. Furthermore, the electron generator comprises a cathode housing and a filament.

In use, an electron beam is generated by heating the filament. When an electrical current is set through the filament, the electrical resistance of the filament causes the filament to be heated to a temperature in the order of 2.000° C. This heating causes the filament to emit a cloud of electrons. The electrons are accelerated towards the electron exit window by means of a high potential difference between the cathode housing and the electron exit window. Subsequently, the electrons paths through the electron exit window and continue towards a target area, e. g. a part of the packaging material that has to be sterilized. The high potential difference is called voltage. It is created by connecting the cathode housing and the filament to the power supply unit providing a high output potential and by connecting the vacuum chamber to ground potential.

Of course other potentials can be used as well, the difference between the potentials give the voltage accelerating the electrons emitted by the filament. Unless otherwise stated the term voltage shall mean the difference between a potential provided by a source and the ground potential. For the purpose of this teaching, electron shall be accelerated from the high potential towards the low potential.

The voltage that is supplied by the power supply unit lies according to one or more embodiments in the range of about 80 to 150 kV. However, higher and lower values are also possible.

An electron beam emitter as described before can be used for sterilization of packaging material, food, biological or medical devices and so on. There are no limitations concerning the content of the packaging material. Thus, the content can be liquid or solid. There are also no limitations concerning the use of the sterilization device or the electron beam emitter itself, respectively. Thus, the electron beam emitter or the sterilization device, respectively, can be used for inside and/or outside sterilization of e. g. packaging material, such as packaging containers.

An electric connection between the power supply unit and the electron beam emitter is provided by a high voltage output connector that is arranged at and/or in the housing of the power supply unit. In particular, as the high voltage components are expediently arranged in the first chamber, the first chamber is connected or connectable, respectively, via the high voltage output connector to the electron beam emitter or to electron beam emitters, respectively. The high voltage output connector provides a connection to the electric system or to at least one electric component/element inside the housing. Generally speaking, the electric system is adapted to generate the high voltage that is necessary to operate the electron beam emitter.

In another embodiment, a special high voltage output connector can be omitted, if the power supply unit and particularly the connection between the power supply unit and the emitter including all wires and connection are properly sealed and the interior of the supply unit is flushed with an insulation gas. To further improve the dielectric strength, a sufficient space in the range of about 20 to 50 mm and particularly bigger than 30 mm should be kept between any cables or supplying the emitter and operating at high voltages and the housing. An hermetic seal is located between the emitter and the housing to maintain the vacuum within the emitter and a pressurized housing.

However, if high voltage is generated, electric insulation is an issue. In particular, corona has to be avoided. Corona discharge is an electrical discharge brought on by the ionization of a medium surrounding a conductor that is electrically energized. Corona discharge is a process by which electrons flow from an electrode with a high potential into an easy ionizable neutral fluid so as to create a region of plasma around the electrode. The ions generated eventually pass charge to nearby areas of lower potential. The discharge will occur when the strength (potential gradient of the electric field) around a conductor is high enough to form a conductive region, but not high enough to cause electrical break down or arching to nearby objects.

However, in the present context also electric arcs or arc discharges have to be avoided as they can damage the power supply unit and its components. With reference to the electric components also surface leakage has to be avoided. In this context, especially the people that work with the sterilization device have to be protected. Therefore, at least one of the electric components is at least partly covered with the solid insulation layer. The use of the solid insulation layer has the advantage that the insulation layer, in other words, the insulation medium, cannot leak out and pollute the material that has to be sterilized.

As already mentioned, the power supply unit is connected or connectable, respectively, to the electron beam emitter. If e. g. oil is used for the electric insulation of the electric system or for parts of the electric system, which has been performed in prior art devices for power supply, maintenance of the sterilization device would be rather difficult. If, for example, the electron beam emitter is demounted from the power supply unit, it has to be absolutely made sure that no insulation oil can leak out of the housing of the power supply unit and pollute the other components of the sterilization machine or the packaging material that has to be sterilized.

Thus, the whole insulation oil has to be extracted before demounting the sterilization device. However, this is expensive and time consuming. Thus, it is a big advantage that the insulation layer is formed, connected, arranged or attached, respectively, directly to the electric component or to the zone of the electric component that has to be electrically insulated. A further advantage is that the insulation layer is a solid insulation layer. This does not mean that the insulation layer must be e. g. hard. The term "solid" just means that the insulation layer is not liquid or gaseous. Thus, the insulation layer can also be soft and flexible etc. Generally, a very exact insulation technique is provided. This means that only these parts of the electric system or of the electric components are covered with the solid insulation layer that do require an electric insulation. It goes without saying that this partial insulation can significantly help to reduce the weight of the whole power supply unit.

As already mentioned, the electric system comprises a plurality of electric components. Each of the electric components can comprise a plurality of electric elements, wherein at least some of the electric elements can be at least partly covered with the solid insulation layer. By way of example, an electric element is for example a circuit board, wherein capacitors and diodes that are arranged at the circuit board are also electric elements. the electric element therefore contains discrete components, but it may also include solid-state electronics and/or integrated circuitry.

According to one or more embodiments the at least one electric component comprises at least one voltage distribution during operation, wherein a zone of the at least one electric component that exceeds (at least) a first voltage threshold is covered with the insulation layer. That has the advantage that only these parts of the electric component(s) or only these electric elements are electrically insulated, which operate in a voltage range exceeding the threshold. According to one aspect of the invention different voltage thresholds can be defined. With respect to the different voltage thresholds different insulation layers or insulation levels, respectively, can be provided. The electric components or at least parts of the electric components are adapted to have different voltages or voltage levels (levels of a different potential) which means that they are for example operated with different voltages or which means that they generate different voltages step wise or continuously.

Expediently, the insulation layer provides a dielectric strength, wherein a value and/or height of the dielectric strength are adjusted by the voltage threshold or wherein the dielectric strength depends on the voltage threshold. This means that the dielectric strength, in other words the insulation level, is the higher the higher is the voltage of the electric component. According to one or more embodiments, material compounds can be used that comprise a plurality of materials like plastics, metals and/or polymer compounds. Examples may comprise epoxy resins, polyester resins, silicones, polypropylenes and liquid organosilicon rubbers, which can also withstand the higher temperatures of such components in operation. Especially for corona prevention a polymer compound with a small amount of conductive additive should be used. Additives may include heat stabilizing additives or conductive additives such a Bariumtitanate, Carbon, nanocomposites with microfillers and the like. Alternatively, the dielectric strength of the insulation layer can be increased by adapting a thickness of the insulations layer(s).

According to one aspect of the invention, the insulation layer comprises epoxy. Alternatively, the at least one insulation layer is made of epoxy. Epoxy has very good insulation properties and provides very good corona suppression if operating time under electromagnetic field is relatively short. However, epoxy can only be used in applications with relatively low electric/electromagnetic fields and low heat dissipation. Thus, epoxy is just used for these electric components/elements that fulfil the aforementioned requirements and/or conditions during operation. As a consequence, according to one or more embodiments the power supply unit is adapted to cool the electric system and/or to minimize the electric and/or electromagnetic field.

In this context it has to be mentioned that the housing of the power supply unit comprises according to one or more embodiments at least one electric insulation shield. The at least one electric insulation shield can be for example made of polyethylene, wherein the at least one insulation shield can be arranged in and/or at the housing of the power supply unit or in and/or at the wall(s) of the housing, respectively. As already mentioned, the use of the at least one insulations shield enables the use of epoxy as material for the insulations layer. If the electric component that exceeds at least the first voltage threshold and that has to be electrically insulated is surrounded by an insulation shield, the electric field can be lowered. As a consequence, epoxy can be used as material for the insulation layer. The insulations shield does not have to be located in and/or at the housing. The insulation shield just has to surround the electric component in a way so that the electric field is lowered in this area.

According to one or more embodiments the housing or the first and the second chamber, respectively, are filled with an insulation medium, in particular an insulation gas, such as nitrogen, carbon dioxide, halogen or vacuum. Nitrogen is a dielectric gas that is adapted to prevent or rapidly quench electric discharges. The insulation medium should be chemically inactive and not cause corrosion of electrical components. The insulation gas in the housing provides an improved dielectric strength of the power supply unit or parts thereof, particular of the already insulated electrical components. Hence the insulation gas supports the solid insulation layer. Another advantage of the use of an insulating gas, such as nitrogen, contrary to the usage of e. g. insulation oil is that a gas cannot leak out and, for example, damage or pollute a material that has to be sterilized. The insulation may also be pressurized within the housing.

Another advantage is the low density of a gas contrary to the density of a liquid insulation material, such as oil. As already mentioned, the sterilization devices are in general arranged at carrousels or the like. These carrousels move very fast and have, for example, to be lifted etc. The weight of the sterilization device should therefore be minimized. This weight reduction can advantageously be realized by the usage of an insulation gas, such as nitrogen. To increase the insulation and cooling properties of the insulation gas, such as nitrogen, the insulation gas is, according to one or more embodiments, dried and/or pressurized. The pressure lies preferably in the range of about 2 to 3 bar above atmospheric pressure, in particular in the range of about 2.5 to 3 bar above the atmospheric pressure.

According to one aspect of the invention the housing or the first and the second chamber, respectively, comprise at least one conveying device, such as a fan. The fan is expediently used to create a circulating gas flow. In particular, a circulating insulation medium flow is generated. In other words, a nitrogen flow is expediently used to cool the electric system. Due to this, the temperature of the electric system or the electric components and its elements, respectively, can be lowered. Such cooling is useful, not only for the electrical components themselves but also for the solid insulation layer, as excessive heat may significantly reduce the dielectric strength of the solid insulation layer. Using additional insulation gas support heat transfer to heat exchange elements and further reduces any corona effect or stray electrons in areas where a strong electrical field is generated. As a result, epoxy or other heat sensitive material can be used for the insulation layer.

According to one or more embodiments the at least one insulation layer is provided by potting. Potting is a process of filling a complete electronic assembly with solid or gelatinous compounds. As already mentioned, preferably epoxy is used. Advantageously, only parts of the electric components are potted.

Alternatively, the at least one electric component is electrically insulated by conformal coating. An advantage of conformal coating is the further reduction of the weight of the power supply unit, as thicknesses of the insulation layers(s) can be made very thin using this technique.

According to one or more embodiments the insulation layer comprises a current conductive additive. A small amount of current conductive additive additionally minimizes the risk of corona and arcs. For example, conductive carbon additives or carbon or stainless steel fibers can be used as current conductive additive. Advantageously, the voltage and/or current distribution within the solid insulation layer can be smoothed. This minimizes the risk of corona and arcs.

According to one or more embodiments the insulation layer comprises a heat conductive additive. As a consequence, the insulation layer can be used to cool the electric components or parts of the electric components, respectively. In addition the heat distribution within the insulation layer can be homogenized. According to one or more embodiments metal particles or power is used as heat conductive additive.

According to one or more embodiments, the insulation layer is connected to a heat absorber unit. The heat absorber unit can be a heat conductive element, in particular a cooled heat conductive element that is adapted to absorb and transfer the heat of the electric component or the insulation layer, respectively. Expediently, the heat conductive element is cooled with a cooling medium, such as water. According to one or more embodiments the heat conductive element is for example at least one plate that is arranged inside the housing, wherein the plate is expediently made of metal, such as aluminum or copper. The plate material should comprise of a high conductivity. The electric system or at least parts of the electric system can be arranged at the plate.

According to one or more embodiments the at least one electric component is a voltage multiplier, wherein the voltage multiplier comprises preferably at least two circuit boards, and wherein the at least two circuit boards are separated from each other. Each of the circuit boards comprises advantageously at least one multiplier stage. According to a preferred embodiment a first circuit board comprises five stages, wherein a second circuit board comprises two stages. Each stage comprises appropriate diodes and capacitors to enable the voltage multiplication. The first circuit board is adapted to multiply an input voltage up to 80 to 90 kV. The second circuit board is adapted to multiply the output voltage of the first circuit board up to 110 or 120 kV (also up to 150 kV). The two circuit boards are connected via an interconnection board, wherein between the interconnection board and the second circuit board there is located a spark current limiter.

Preferably, the spark current limiter as well as the second circuit board is covered with at least one insulation layer. As already mentioned, if operating time under electromagnetic field is relatively short epoxy can be used as material for the insulation layer. This applies to the spark current limiter.

Due to very low power dissipation of the last stages of the second circuit board epoxy can be used as material for the insulation layer.

Expediently, a multiplier current of stage lies within a range of about 7 to 10 mA, wherein the multiplier current of stage lies within a range of about 20 mA. For comparison, the multiplier current of the first stage lies within a range of about 70 mA. This causes approximately 10 times more heat dissipation. The use of epoxy would not be possible. According to one aspect of the invention, the second circuit board as well as the spark current limiter is additionally electrically insulated by the insulation shield that is arranged at and/or in the housing of the power supply unit, at least in the range of an area or zone of the second circuit board. Due to this, the electric/electromagnetic field can be lowered or reduced in this area or zone which enables the use of epoxy as material for the insulation layer. It goes without saying that the voltage multiplier can also comprise just one circuit board or more than two circuit boards. Generally, the last steps of the voltage multiplier generate very low power dissipation which advantageously enables the use of epoxy as material for the insulation layer.

According to one or more embodiments the insulation layer comprises an inner surface and an outer surface, wherein a minimal radius that is formed by the outer surface is bigger than about 3 mm. As corona is also a function of the radius of a curvature of a conductor, the form of the outer surface is also an issue. Therefore, regardless of whether potting or conformal coating is used, the form of the outer surface of the insulation layer should not have sharp edges or too small radiuses.

According to the invention a sterilization device, in particular for packaging material, comprises a power supply unit and at least one electron beam emitter, wherein the power supply unit comprises at least one electric component, characterized in that at least one of the electric components is at least partly covered with a solid insulation layer.

According to the invention, an electric component, in particular a voltage multiplier comprises at least one voltage distribution, characterized in that a zone of the electric component that exceeds a first voltage threshold is covered with a solid insulation layer, wherein the solid insulation layer is adapted to electrically insulate the zone.

The power supply unit according to the invention can include the features and advantages of the sterilization device according to the invention and of the electric component according to the invention and vice versa.

Additional aspects and features of the current invention are shown in the following description of preferred embodiments of the current invention with reference to the attached drawings. Single features or characteristics of respective embodiments are explicitly allowed to be combined within the scope of the current invention.

Figure 1A:
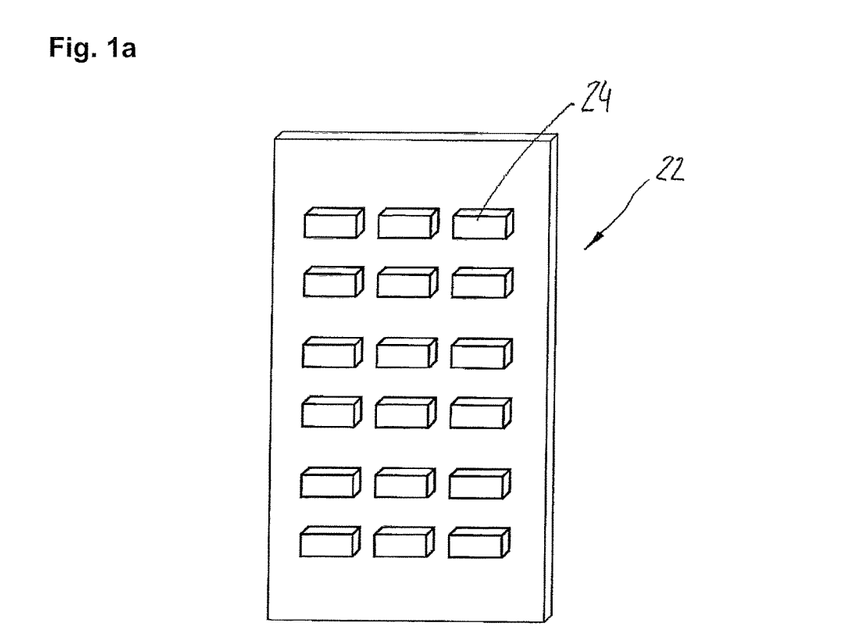
FIG. 1a: shows an electric component without an insulation layer.

Referring now to FIG. 1a an electric component 22 is shown. The electric component 22 comprises a plurality of electric elements 24.

Figure 1B:
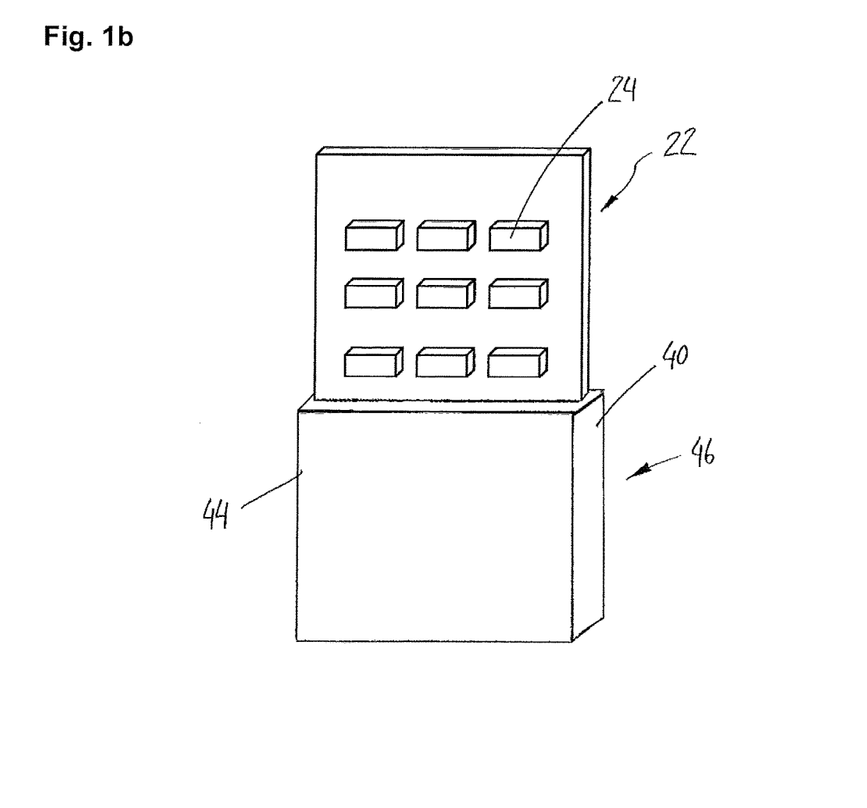
FIG. 1b: shows according to one or more embodiments an electric component that is electrically insulated by potting.

FIG. 1b shows an insulation layer 46 arranged partly over electric component 22. Electric elements 24, which operate, create or handle potential or voltages exceeding at least a first voltage threshold are covered by solid insulation layer 40. The solid insulation layer 40 is provided by potting. The solid insulation layer 40 comprises an outer surface 44, which substantially flat and an inner surface. The inner surface of solid insulation layer 40 is at least partly in contact with the electric component 22. The upper area of the electric component 22 is not covered by insulation layer 46, as the components arranged in that area do not operate, create, use or handle voltages exceeding the first voltage threshold. In this case, an additional solid insulation layer is not necessary.

Figure 1C:
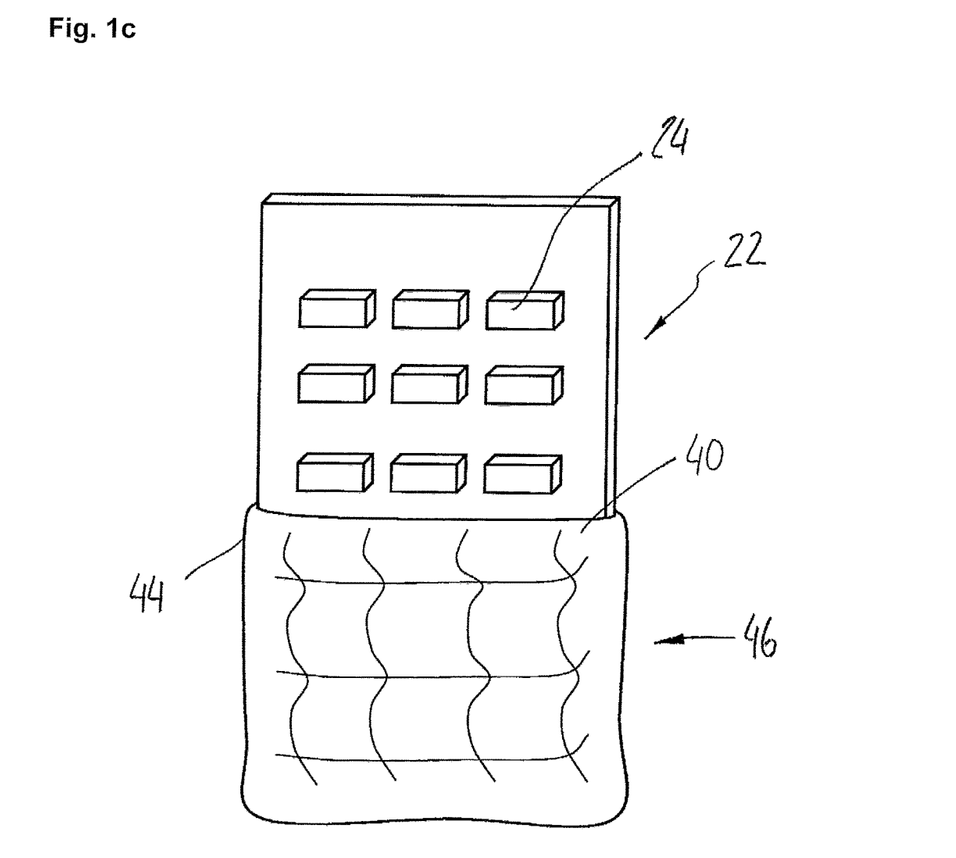
FIG. 1c: shows according to one or more embodiments an electric component that is electrically insulated by conformal coating.

FIG. 1c illustrates the electric component 22 that is already known from FIGS. 1a and 1b. A zone 46 that exceeds a first voltage threshold is covered by a solid insulation layer 40, wherein the solid insulation layer 40 is provided by conformal coating. As a result the coating follows the shape of the electrical elements 24 arranged on the board.

Figure 2:
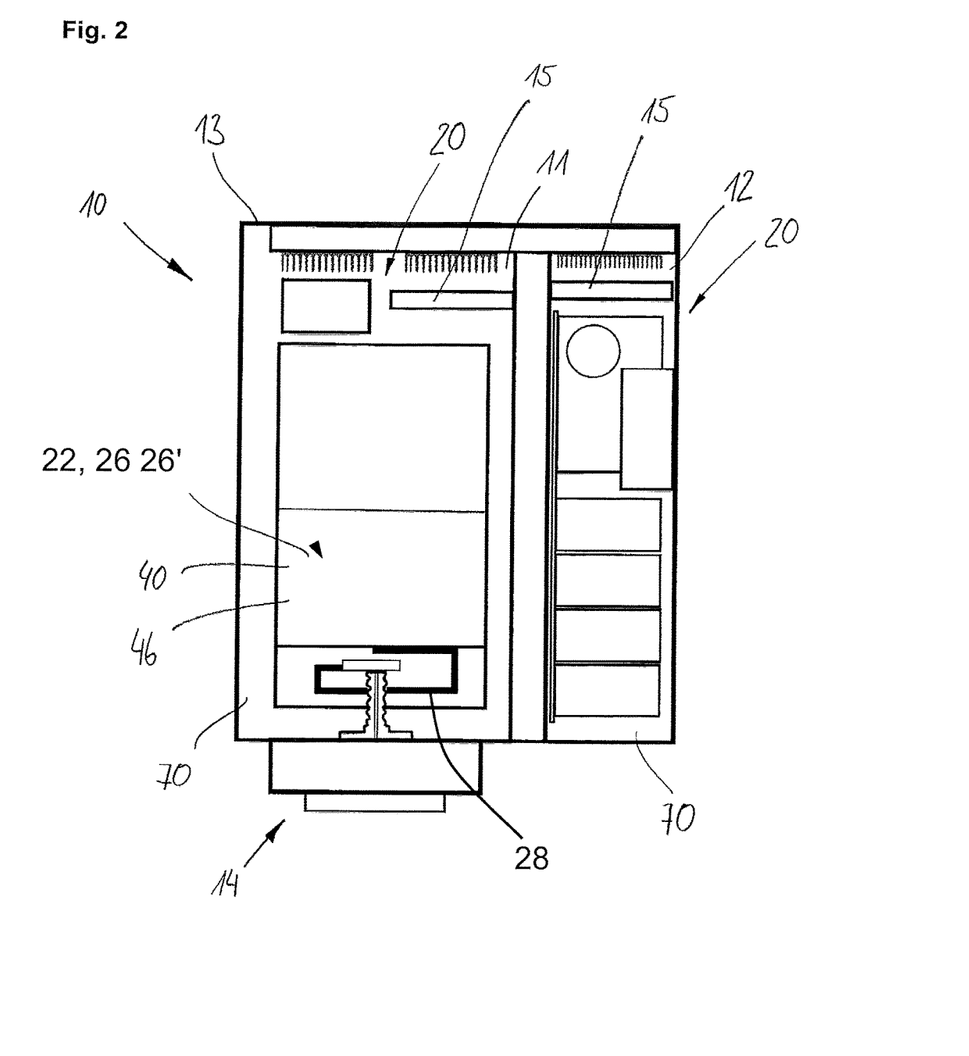
FIG. 2: shows according to one or more embodiments a power supply unit comprising an electric system.

FIG. 2 shows a power supply unit 10 according to an embodiment. The power supply unit 10 comprises a housing 13, wherein the housing 13 is separated into a first chamber 11 and a second chamber 12. Both chambers 11, 12 comprise fans 15 that are adapted to cool the electric system 20 arranged inside the housing. Expediently, the chambers 11, 12 are filled with an insulation medium 70, in particular an insulation gas, such as nitrogen. The insulation medium 70 is also used for cooling of the electric system 20, e. g. using the fans 15. The solid insulation layers 40 of the electric system 20 are cooled by medium 70.

However, the electric system 20 comprises usually control system components, power components and high voltage components, wherein the control system components and control components are expediently arranged in the second chamber 12 and wherein the high voltage components, as for example a voltage multiplier 22, is arranged expediently in the first chamber 11. The voltage multiplier 22 is connected to a high voltage output connector 14 that is adapted for a connection to an electron beam emitter (not shown). The voltage multiplier 22 as shown in FIG. 2 comprises a first circuit board 26'. A zone 46 of the voltage multiplier 22 that exceeds at least a first voltage threshold is covered with a solid insulation layer 40. Expediently, also a spark current limiter 28 is covered with an insulation layer (not shown). According to one or more embodiments the threshold lies within a range of about 80 to 90 kV. An output voltage of the voltage multiplier 20 lies according to one or more embodiments in the range of about 110 to 120 kV (also up to 150 kV).

Figure 3:
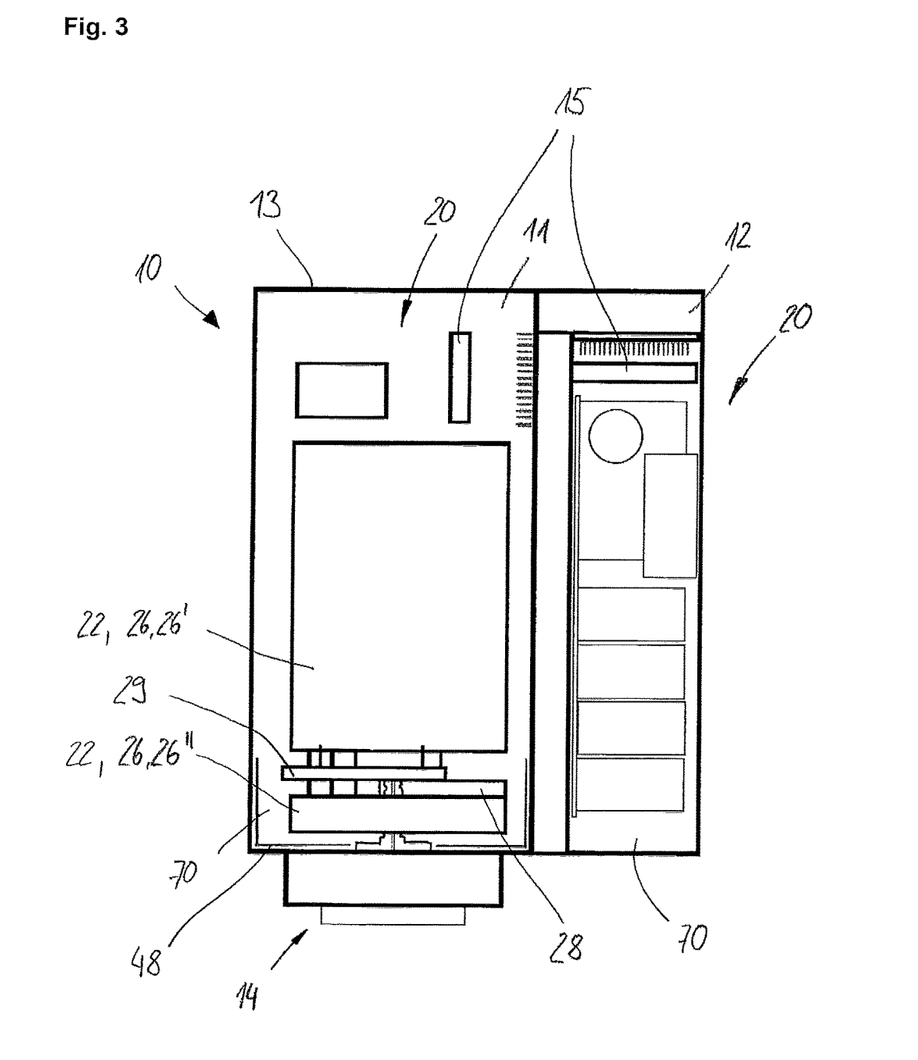
FIG. 3: shows a further embodiment of a power supply unit.

FIG. 3 shows a further embodiment of a power supply unit 10. This embodiment is similar to the one shown in FIG. 2. However, a voltage multiplier 22 comprises a first circuit board 26' and a second circuit board 26". The two circuit boards 26' and 26" are connected via an interconnection board 29. Between the interconnection board 29 and the second circuit board 26" a spark current limiter 28 is arranged. Each of the circuit boards 26', 26" comprises advantageously at least one multiplier stage. According to one or more embodiments the first circuit board 26' comprises five stages, wherein the second circuit board 26" comprises two stages.

Each stage comprises appropriate diodes and capacitors to enable the voltage multiplication (not shown). The first circuit board 26' is adapted to multiply an input voltage up to 80 to 90 kV. The second circuit board 26" is adapted to multiply the output voltage of the first circuit board up to 110 or 120 kV (also up to 150 kV). FIG. 3 shows that the second circuit board 26" and the spark current limiter 28 are additionally electrically insulated by an insulation shield 48. The insulation shield 48 is arranged and/or attached at and/or in the wall(s) of the housing 13. According to one or more embodiments, the insulation shield 48 is made of polyethylene. The insulation shield 48 has the advantage that an electric field in the area of the second circuit board 26" can be lowered. This enables the use of epoxy for the material for the solid insulation layer. The remaining features are similar to these shown and explained in FIG. 2.

Figure 4A:
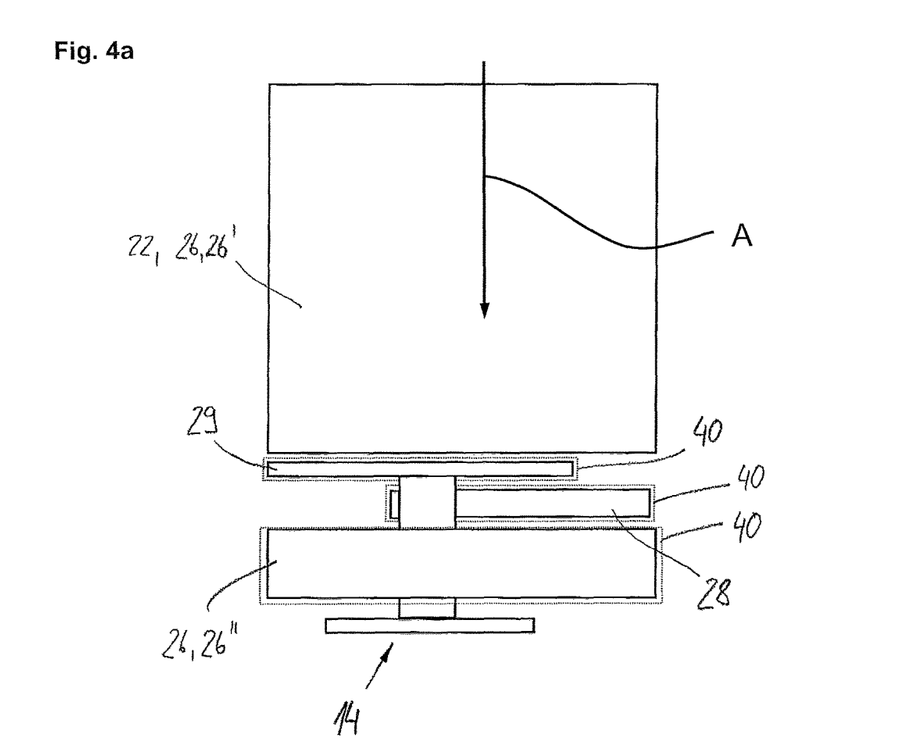
FIG. 4a: shows an embodiment of a voltage multiplier.

FIG. 4a shows an embodiment of a voltage multiplier used in a power supply unit as illustrated in FIG. 3. As can be seen from FIG. 4a, the interconnection board 29, the spark current limiter 28 and the second circuit board 26" are electrically insulated by a solid insulation layer 40. Potting can be used to create the solid insulation layer 40. Alternatively or at least partly also conformal coating may be used. According to one or more embodiments the material that is used for the solid insulation layer 40 is epoxy.

Figure 4B:
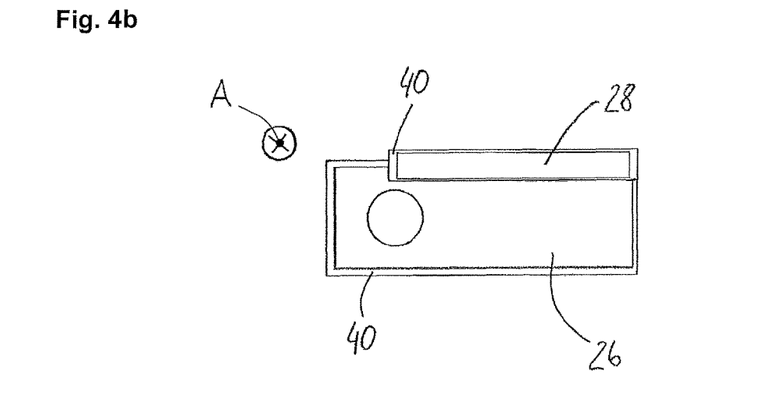
FIG. 4b: shows the embodiment of FIG. 4a in a view along an axis A.

FIG. 4b shows the embodiment of FIG. 4a in a view along the axis A. To be exact, a sectioning is shown so that the spark current limiter 28 and the lower part of the voltage multiplier 26 (in particular the second circuit board 26") can be seen from above. Thus, a position of the spark current limiter 28 relating to the voltage multiplier 26 can be seen. The voltage multiplier 26 comprises a hole that is adapted to arrange the high voltage output connector 14 (not shown in FIG. 4b). The spark current limiter 28 and the voltage multiplier are covered with the solid insulation layer 40.

Figure 5:
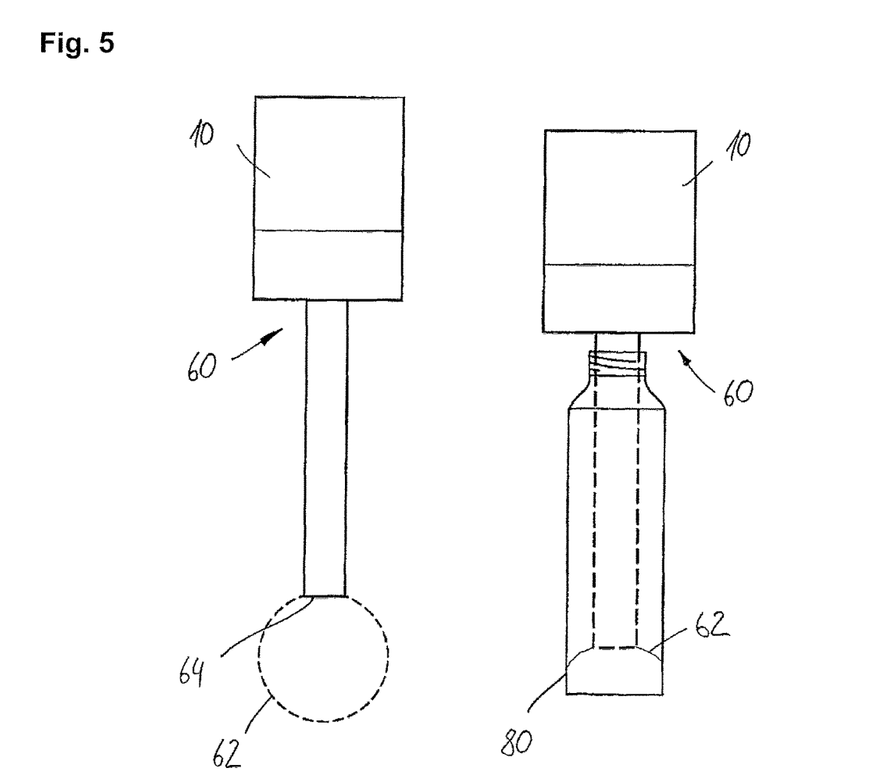
FIG. 5: shows an embodiment of an electron beam emitter.

FIG. 5 shows a principle scheme of an embodiment of a sterilization device comprising a power supply unit 10 and an electron beam emitter 60. The electron beam emitter 60 comprises an electron exit window 64, wherein an electron cloud 62 is formed during sterilization. The electron cloud 62 is for example used for inside sterilization of a packaging material 80, in particular a packaging container 80 (e. g a carton packaging container) as can be seen on the right.

Figure 6:
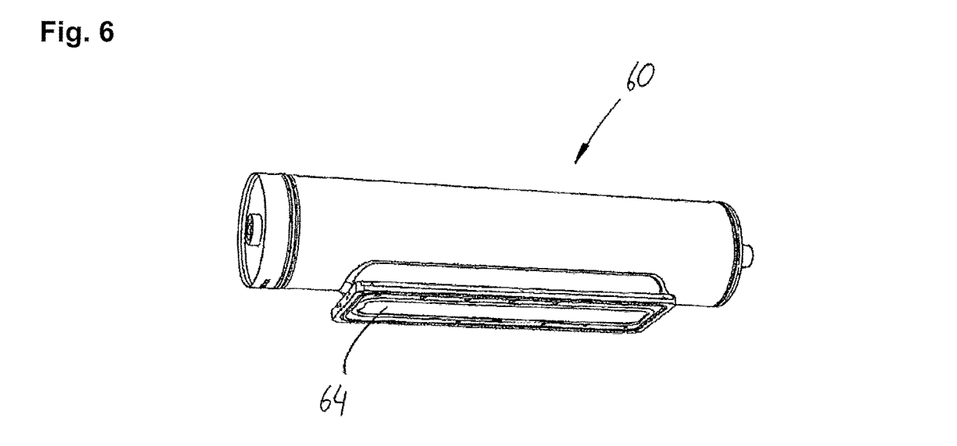
FIG. 6: shows a further embodiment of an electron beam emitter.

FIG. 6 shows another embodiment of an electron beam emitter 60 comprising an electron exit window 64. The electron beam emitter 60 as shown in FIG. 6 is for example used for outside sterilization of packaging material, in particular packaging containers, or for sterilization of flat and/or plane materials or devices.

REFERENCE NUMERALS

10 power supply unit
11 first chamber
12 second chamber
13 housing
14 high voltage output connector
15 fan
20 electric system
22 electric component
24 electric elements
26 voltage multiplier
26' first circuit board
26" second circuit board
28 spark current limiter
29 interconnection board
40 solid insulation layer
44 outer surface
46 zone that exceeds a first voltage threshold
48 insulation shield
60 electron beam emitter
62 electron cloud
64 electron exit window
70 insulation medium
80 packaging material

The invention claimed is:

1. Sterilization device for packaging material comprising:
a power supply unit and at least one electron beam emitter, the power supply unit comprising:
a housing;
at least one electric component disposed within the housing and configured to provide an output voltage to a high voltage output connector,
at least one of the electric components is at least partly covered with a solid insulation layer that provides electric insulation to the at least one of the electric component, and
the solid insulation layer comprising epoxy,
wherein the at least one electric component comprises at least a first element configured to operate at a first voltage and a second element configured to operate at a second voltage, said second voltage being lower than the first voltage, a zone of the at least one electric component that encompasses the at least first element being covered with the solid insulation layer.

2. Sterilization device according to claim 1, wherein the solid insulation layer provides a dielectric strength, and a value of the dielectric strength being selected in dependence of a first voltage.

3. Sterilization device according to claim 1, wherein the housing comprises at least one electric insulation shield.

4. Sterilization device according to claim 1, wherein the solid insulation layer comprises a current conductive additive.

5. Sterilization device according to claim 1, wherein the solid insulation layer comprises a heat conductive additive.

6. Sterilization device according to claim 1, wherein the solid insulation layer is connected to a heat absorber unit.

7. Sterilization device according to claim 1, wherein the solid insulation layer comprises an inner surface and an outer surface, the outer surface possessing a radius bigger than about 3 mm.

8. Sterilization device according to claim 1, wherein the solid insulation layer is connected to a heat sink.

9. Sterilization device according to claim 1, wherein at least a part of the one electric component is exposed outside the solid insulation layer.

10. Sterilization device for packaging material comprising:
a power supply unit and at least one electron beam emitter, the power supply unit comprising:
a housing;
at least one electric component disposed within the housing and configured to provide an output voltage to a high voltage output connector; and
at least one of the electric components is at least partly covered with a solid insulation layer that provides electric insulation to the at least one of the electric component;

wherein the solid insulation layer comprises epoxy; and
wherein the at least one electric component is a voltage multiplier, and wherein the voltage multiplier comprises two circuit boards.

11. Sterilization device according to claim 10, wherein the housing comprises at least one electric insulation shield.

12. Sterilization device according to claim 10, wherein the solid insulation layer comprises a current conductive additive.

13. Sterilization device according to claim 10, wherein the solid insulation layer comprises a heat conductive additive.

14. Sterilization device according to claim 10, wherein the solid insulation layer is connected to a heat sink.

15. Sterilization device for packaging material comprising:
a power supply unit and at least one electron beam emitter, the power supply unit comprising:
a housing;
at least one electric component disposed within the housing and configured to provide an output voltage to a high voltage output connector; and
at least one of the electric components is at least partly covered with a solid insulation layer that provides electric insulation to the at least one of the electric component;
wherein the solid insulation layer comprises epoxy; and
wherein the at least one electric component comprises a first element which operates at a first voltage and a second element which operates at a second voltage, the second voltage being lower than the first voltage, the first element being covered by the solid insulation layer, the second element being exposed outside the solid insulation layer.

16. Sterilization device according to claim 15, wherein the housing comprises at least one electric insulation shield.

17. Sterilization device according to claim 15, wherein the solid insulation layer comprises a current conductive additive.

18. Sterilization device according to claim 15, wherein the solid insulation layer comprises a heat conductive additive.

19. Sterilization device according to claim 15, wherein the solid insulation layer is connected to a heat sink.

* * * * *